(12) United States Patent
Bonastre et al.

(10) Patent No.: US 7,344,711 B2
(45) Date of Patent: Mar. 18, 2008

(54) USE OF ADENOVIRUSES MUTATED IN THE VA GENES FOR CANCER TREATMENT

(75) Inventors: Ramon Alemany Bonastre, Barcelona (ES); Manel Maria Piqueras, Barcelona (ES)

(73) Assignee: Oncolytics Biotech Inc., Calgary, Alberta (CA)

( * ) Notice: Subject to any disclaimer, the term of this patent is extended or adjusted under 35 U.S.C. 154(b) by 346 days.

(21) Appl. No.: 10/509,194

(22) PCT Filed: Mar. 25, 2003

(86) PCT No.: PCT/ES03/00140

§ 371 (c)(1),
(2), (4) Date: Sep. 23, 2004

(87) PCT Pub. No.: WO03/080083

PCT Pub. Date: Oct. 2, 2003

(65) Prior Publication Data

US 2006/0233753 A1 Oct. 19, 2006

(30) Foreign Application Priority Data

Mar. 26, 2002 (ES) ............... 200200716

(51) Int. Cl.
*A61K 48/00* (2006.01)
*C12N 15/861* (2006.01)

(52) U.S. Cl. .................. 424/93.2; 435/320.1

(58) Field of Classification Search ............ None
See application file for complete search history.

(56) References Cited

U.S. PATENT DOCUMENTS

| 5,002,874 | A | 3/1991 | Kaufman |
| 5,981,225 | A | 11/1999 | Kochanek et al. |
| 6,254,862 | B1 * | 7/2001 | Little et al. ............... 424/93.2 |
| 2004/0132675 | A1 * | 7/2004 | Kuo et al. ............... 514/44 |
| 2006/0233753 | A1 * | 10/2006 | Bonastre et al. ............ 424/93.2 |

FOREIGN PATENT DOCUMENTS

| WO | 98/35028 | 8/1998 |
| WO | WO99/57296 | 11/1999 |
| WO | 01/35970 | 5/2001 |

OTHER PUBLICATIONS

Zhao et al., "Absence of virus-associated (VA) RNA coding regions in canine adenoviral genomes," Bingdu Xuebo 13(1):54-58, 1997, Abstract only.*
Thimmappaya et al., "Adenovirus VAI RNA is required for efficient translation of viral mRNAs at late times after infection," Cell 31: 543-551, 1982.*
Alemany et al., "Replicative adenoviruses for cancer therapy", *Nature Biotechnology* 18, 723-727, 2000.
Bergmann et al., "A genetically Engineered Influenza A Virus with ras-Dependent Oncolytic Properties", *Cancer Research*, 61: 8188-8193, 2001.
Fowlkes et al., "Transcriptional Control Regions of the Adenovirus VAI RNA Gene" *Cell* 22, 405-413, 1980.
Fueyo et al., "A Mutant oncolytic adenovirus targeting the Rb pathway produces anti-glioma effect in vivo", *Oncogene* 19, 2-12, 2000.
Gunnery et al. "Termination Sequence Requirements Vary among Genes Transcribed by RNA polymerase III" *Journal of Molecular Biology* 286 745-757, 1999.
Ma et al. "Sturcture, Funcsion, and Evolution of Adenovirus-Associated RNA: a Phylogenetic Approach", *Journal of Virology* 70(8), 5083-5099, 1996.
Mundschau et al., "Oncogenic *ras* Induces an Inhibitor of Double-stranded RNA-dependent Eukaryotic Initiation Factor 2α-kinase Activation", *Journal of Biological Chemistry*, 267(32):23092-23098, 1992.
Norman et al., "Reovirus as a novel oncolytic agent", *Journal of Clinical Investigation* 105: 1035-1038, 2000.
Stojdl et al., "Exploiting tumor-specific defects in the interferonpathway with a previously unknown oncolytic virus", *Nature Medicine* 6)7): 821-825, 2000.
Cascallo et al., "Deletion of VAI and VAII RNA genes in the design of oncolytic adenoviruses," Hum. Gene Ther. 17(9):929-40 (2006).
Furtado et al., "Functional dissection of adenovirus VAI RNA," J. Virol. 63(8):3423-3434 (1989).

* cited by examiner

*Primary Examiner*—Scott D. Priebe
(74) *Attorney, Agent, or Firm*—Fish & Richardson P.C.

(57) ABSTRACT

This invention refers to the use of an adenovirus for cancer treatment, being this adenovirus defective in its virus-associated (VA) RNAs. Said adenovirus has a mutation in the VAI or VAII gene sequence or both. This adenovirus may also have mutations in the sequences controlling expression of the VA RNAs.

15 Claims, 6 Drawing Sheets

FIGURE 2

```
CGGACGCGGT TCCAGATGTT GCGCAGCGGC AAAAAGTGCT CCATGGTCGG
GACGCTCTGG CCGGTCAGGC GCGGCGCAATC GTTGACGCTC TAGACCGTGC
AAAAGGAGAG CCTGTAAGCG GGCACTCTTC CGTGGTCTGG TGGATAAATT
CGCAAGGGTA TCATGCCGGA CGACCGGGGT TCGAGCCCCG TATCCGGCCG
TCCGCCGTGA TCCATGCCGGT TACCGCCCGC GTGTCGAACC CAGGTGTGCG
ACGTCAGACA ACGGGGGAGT GCTCCTTTTG GCTTCCTTCC AGGGCGGGCG
GCTGCTGCGC TAGCTTTTTT GGCCACTGGC CGCGGCCAGC GTAAGCGGTT
AGGCTGGAAA GCGAAAGCAT TAAGTGGCTC GCTCCCTGTA GCCGGAGGGT
TATTTTCCAA GGGTTGAGTC GCGGGACCCC CGGTTCGAGT CTCGGACCGG
CCGGACTGCG GCGAACGGGG GTTTGCCTCC CCGTCATGCA AGACCCCGCT
TGCAAATTCC TCCGGAAACA GGGACGAGCC CCTTTTTTGC TTTTCCAGA
TGCATCCGGT GCTGCGGGCAG ATGCGCCCCC CTCCTCAGCA GCGGCAAGAG
```

FIGURE 4
Transfection of 293 with { V12 H-ras (constitutively active)
N17 H-ras (negative dominant)
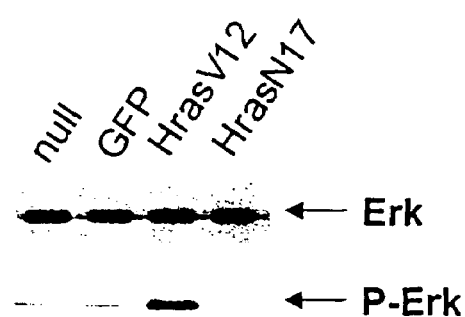
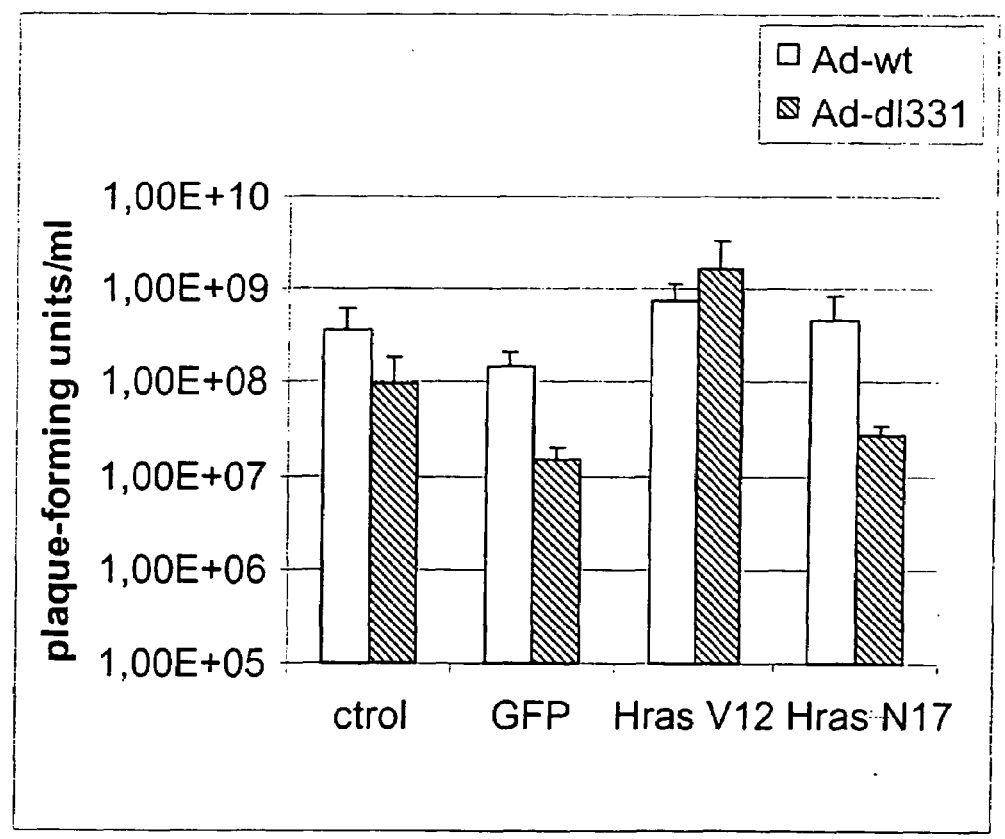

SEQUENCE LISTING

```
<160> NUMBER OF SEQ ID NOS: 2

<210> SEQ ID NO 1
<211> LENGTH: 160
<212> TYPE: RNA
<213> ORGANISM: Human adenovirus type 5

<400> SEQUENCE: 1
gggcacucuu ccguggucug guggauaaau ucgcaagggu aucauggcgg acgaccgggg      60
uucgagcccc guauccggcc guccgccgug auccaugcgg uuaccgcccg cgugucgaac     120
ccaggugugc gacgucagac aacgggggag ugcuccuuuu                            160

<210> SEQ ID NO 2
<211> LENGTH: 600
<212> TYPE: DNA
<213> ORGANISM: Human adenovirus type 5

<400> SEQUENCE: 2
cggacgcggt tccagatgtt gcgcagcggc aaaaagtgct ccatggtcgg gacgctctgg      60
ccggtcaggc gcgcgcaatc gttgacgctc tagaccgtgc aaaaggagag cctgtaagcg     120
ggcactcttc cgtggtctgg tggataaatt cgcaagggta tcatggcgga cgaccggggt     180
tcgagccccg tatccggccg tccgccgtga tccatgcggt taccgcccgc gtgtcgaacc     240
caggtgtgcg acgtcagaca acgggggagt gctccttttg gcttccttcc aggcgcggcg     300
gctgctgcgc tagcttttttt ggccactggc cgcgcgcagc gtaagcggtt aggctggaaa     360
gcgaaagcat taagtggctc gctccctgta gccggagggt tattttccaa gggttgagtc     420
gcgggacccc cggttcgagt ctcggaccgg ccggactgcg gcgaacgggg gtttgcctcc     480
ccgtcatgca agacccccgct tgcaaattcc tccggaaaca gggacgagcc cctttttttgc     540 ttttcccaga tgcatccggt gctgcggcag atgcgccccc ctcctcagca gcggcaagag     600
```

USE OF ADENOVIRUSES MUTATED IN THE VA GENES FOR CANCER TREATMENT

CLAIM OF PRIORITY

This application is a National Stage Application of International Patent Application No. PCT/ES03/00140, filed on Mar. 25, 2003, and claims the benefit of Spanish Patent Application Serial No. ES200200716, filed on Mar. 26, 2002.

AIM OF THE INVENTION

The field of the invention relates in general terms to the field of tumor biology. In particular, the invention refers to mutated adenoviruses in VA RNA genes and their use in inhibiting cancer.

STATUS OF THE PRIOR ART

Current cancer treatment is based mainly on chemotherapy, radiation therapy, and surgery. In spite of a high cure rate for early stages of cancer, most advanced cases of cancer are incurable because they cannot be surgically removed or because the doses of radiation or chemotherapy administered are limited by their toxicity to normal cells. The transfer of genetic material to inhibit or destroy tumors is a very promising therapeutic alternative. Compared to conventional strategies, this gene therapy strategy seeks to target malignant cells more specifically, attacking genetic defects in tumor cells. There are several strategies that use DNA as a therapeutic agent: the transfer of genes that stimulate antitumor immune response, the transfer of toxic genes that activate the toxicity of drugs, and the transfer of DNA to block or reestablish the expression of genes involved in tumor development (oncogenes, tumor suppressor genes, antiangiogenic genes, etc.) In addition to therapeutic DNA, the other component of gene therapy is the vehicle that transports this DNA: the vector. Synthetic vectors and viral derivatives have been used to increase the transfer of DNA to the target cells. The latter are generally more efficient in transferring DNA or transducing tumor cells. Viral vectors have been developed from various types of viruses, including retroviruses, Herpes Simplex virus, adeno-associated viruses, and adenoviruses, among others. In cancer gene therapy, the adenovirus is preferred for its high capacity to infect epithelial cells, which are the cause of most solid tumors. Other advantages of adenoviral vectors are that the DNA can be transferred to cells not yet in division, that the vector DNA is not integrated into the genome of the transduced cell, that these vectors can be purified up to concentrations of 1013 viral particles per milliliter, and that they are stable in the bloodstream because they lack lipid envelopes.

The adenovirus is a DNA virus without a lipid envelope, characterized by an icosahedral capsid enclosing a linear, double-stranded DNA of approximately 36 kilobases. There are 50 serotypes of human adenovirus, which are classified into six subgroups (A to F) based on their structural and functional properties, such as erythrocyte agglutination. In gene therapy, adenovirus type 5 is preferred because it is molecularly well defined and because of its low pathogenicity in humans. In fact, 85% of the population has been infected with adenovirus and is seropositive for the presence of adenovirus antibodies. In particular, type 5 adenovirus causes colds in children that in most cases are asymptomatic.

Various E1-deleted adenoviral vectors have been used with little success to treat cancer in clinical trials. Their limited effectiveness is due to the scant number of cells that the vector reaches. The large size of the viral particle, 80 nm in diameter, makes it difficult to diffuse and the vector reaches only a few layers or tumor cells beyond the injection site or the blood vessels. This limitation is particularly relevant in therapeutic strategies based on the introduction of cytotoxic genes or tumor suppressors, in spite of the fact that a collateral cytotoxic effect was found in nontransduced cells that were near transduced ones. Even when multiple high doses of the vector were injected, most of the tumor cells remained unaffected by the vector. In recent years, the selective propagation of the vector in tumor cells has been proposed as strategy to solve this limitation (R. Alemany et al., Nature Biotechnology 2000, Vol. 18, pp. 723-7). Viral replication per se is cytopathic; therefore, cytotoxic genes or tumor suppressors are not necessary to obtain an antitumor effect. In a way, the concept of an adenovirus that selectively replicates itself in tumor cells without carrying a nonviral gene belongs more precisely to the field of viral therapy or virotherapy of cancer than to the field of gene therapy. However, since cytotoxic genes, immunostimulants, or tumor suppressors may increase the selective toxicity of the replicative adenovirus; said genes have been inserted into the genome of the replicative adenovirus. These selective replication vectors thus link the concepts of virotherapy and gene therapy.

Virotherapy, or the use of viruses in cancer treatment, is much older than gene therapy. The first observations of tumor treatments using viruses date from the beginning of the last century. Some viruses are naturally oncotropic. For example, parvovirus replication seems to be linked to the malignant transformation of the cell by a mechanism that is still unknown. The vesicular stomatitis virus (VSV) has an oncotropism associated with the antiviral effects of interferon. VSV is very sensitive to inhibition by interferon and tumor cells are often unresponsive to the effects of interferon, causing them to have a deficient antiviral response. Another virus that has been identified recently as oncotropic is the reovirus (Norman and Lee, Journal of Clinic Investigation, 2000. Vol. 105, pp. 1035-8). Infected cells react to the production of double-strand RNA (dsRNA) produced during infection with reovirus or other viruses activating a dsRNA-dependent kinase (PKR). The PKR, thus activated, blocks protein synthesis through the phosphorylation of the alpha unit of the eIF2 translation factor. This block of the messenger RNA translation also blocks the viral RNA translation and, with it, replication of the virus. Many types of virus express genes that render the PKR inactivate, but not the reovirus. However, PKR can be rendered inactivated by other proteins found in the Ras signal transduction pathway. Therefore, in cells with an active Ras, as in the case of many tumor cells, the reovirus can propagate. Other viruses show no natural oncotropism but can be genetically manipulated so that they replicate selectively in tumors. For example, the Herpes Simplex virus (HSV) has been made oncotropic by deleting the ribonucleotide reductase gene, an enzymatic activity dispensable in cells in active proliferation, such as tumor cells. HSV has also been made oncotropic by deleting the protein ICP34.5, which counteracts the active translation block by the PKR. Its deletion results in an oncotropism by a mechanism similar to that of the revirus. Recently, the Influenza A virus has been manipulated to be oncotropic (Bergmann et al., Cancer Research 2001, Vol. 61, pp. 8188-93). The viral protein NS1 of this virus also counteracts the translation block by PKR and its deletion results in a virus that depends on an active Ras. However, it is with adenoviruses that the most genetic manipulations have been performed to obtain selective replication in tumors. The central role of adenoviruses in cancer gene therapy, together with the experience accumulated in clinical trials, has contributed to the popularity of these new replicative adenoviral vectors.

Two methods have been used to restrict adenovirus replication to tumor cells: the replacement of viral promoters with tumor selective promoters and deletion of viral functions that are unnecessary in tumor cells. In both strategies, the preferred gene to be regulated or mutated is E1a because it controls the expression of the remaining genes. Many tissue- or tumor-specific promoters have been used to control E1a expression. With respect to the strategy of deleting viral functions that are unnecessary in tumor cells, the first mutant proposed for selective replication had a E1b-55K deletion. This protein binds with and inactivates p53 to induce the infected cell to enter the S-phase of the cell cycle and to inhibit p53-mediated apoptosis triggered as a result of this induction. An adenovirus with an E1b-55K mutation known as dl1520 or Onyx-015 has been used to treat tumors with p53 defects. Another mutation performed on the adenovirus genome to obtain selective replication in tumors affects the CR1 and CR2 domains of E1a. These domains of E1a mediate the binding of proteins in the Retinoblastoma (RB) family. The RB proteins block the transition from the Go/G1 phase to the S phase of the cycle, forming a complex inhibitor of the transcription together with E2F. When E1a binds with RB, the E2F transcription factor is released from the RB-E2F complex and E2F acts as a transcription activator of the genes responsible for the transition to the S phase and viral genes such as E2. The release of E2F is thus a key step in the replication of the adenovirus. In tumor cells, the cell cycle is out of control because the RB is absent or inactivated by hyperphosphorylation and E2F is released. In these cells, the RB-inactivating function of E1a is no longer needed. Therefore, an adenovirus with an E1a mutant that prevents binding with the RB can be propagated normally in cells with inactive RB. The selective replication of these mutants has been demonstrated (Fueyo et al., Oncogene 2000, Vol. 19, pp. 2-12).

This invention describes a new type of mutation for achieving selective replication in tumor cells with a determined genetic defect that is distinct from the p53 and RB pathways. Unlike other constructions existing in the field, in this invention the target DNA of the mutation does not produce any viral protein, but a virus-associated (VA) RNA, and it does not belong to the early adenovirus genes but to the late ones. Without any experimental data, WO 01/35970 mentions the use of a modified adenovirus in which the VAI gene is not transcribed; however, in regard to this technique, the combined use of adenoviruses with simultaneous mutations of the VAI gene and the VAII gene has never been mentioned. The genetic defect being attacked in this invention is the signal transduction pathway of the Ras oncogene, a pathway that has not been previously attacked with adenovirus. Many growth factor receptors activate Ras proteins (H-Ras, N-Ras, K-Ras A and K-Ras B) to transduce a proliferative signal from the cell's exterior to the nucleus. Ras proteins are small GTPases that, when bound to GTP, are able to activate a series of effectors. The activation of the effectors creates a mitogenic signal. Ras is mutated into a permanently active form in 90% of pancreas tumors, 50% of colon tumors, 30% of lung tumors, and in other proportions in many other types of tumors. In addition to a large number of tumors with mutated Ras, the Ras pathway is activated in other cases by the constitutive activation of Ras-regulating proteins or vectors of the Ras pathway. For example, the c-erbB gene that encodes the EGF receptor is overexpressed in 50% of glioblastomas and its homologue c-erbB2 is frequently overexpressed in breast and ovarian cancer. Generally speaking, it is considered that 80% of tumors have an activated Ras pathway. Many of these types of tumors, as in the case of pancreatic cancer, need new therapies given the lack of response to conventional therapy.

DESCRIPTION OF THE INVENTION

This invention refers to the use of an adenovirus defective in its VAI and VAII virus-associated RNAs for the treatment of cancer.

It also refers to the use of an adenovirus for the treatment of cancer wherein said adenovirus has a mutation in the sequences of the VAI and VAII RNA genes.

Another objective of the invention is the use of an adenovirus for the treatment of cancer wherein said adenovirus has a mutation in the sequences of the genes that control the expression of the VAI and VAII RNA genes.

Another objective of the invention is the use of an adenovirus for the treatment of cancer wherein said adenovirus has mutations in the VA RNA genes in one or more genes of the group E1a, E1b, and E4 to obtain selective replication in tumors.

Another objective of the invention is the use of an adenovirus for the treatment of cancer wherein said adenovirus has mutations in the VA RNA genes and promoters that regulate one or more genes in the group E1a, E1b, and E4 to obtain selective replication in tumors.

Yet another objective of this invention is the use of an adenovirus for the treatment of cancer wherein said adenovirus has mutations in the VA RNA genes to obtain selective replication in tumor cells with an active Ras pathway or unresponsive to the action of interferon.

Yet another objective of this invention is the use of an adenovirus for the treatment of cancer wherein said adenovirus has mutations in the VA RNA genes to obtain selective replication in tumor cells and modifications in its capsid to increase its infectivity or to direct it to a receptor present on a tumor cell.

Yet another objective of this invention is the use of an adenovirus for the treatment of cancer wherein said adenovirus has mutations in the VA RNA genes that confer selective replication on tumor cells and that, in turn, contain other genes commonly used in the field of cancer gene therapy such as prodrug activators, tumor suppressors, or immunostimulants.

Yet another objective of this invention is the use of an adenovirus for the treatment of cancer wherein said adenovirus is a human adenovirus derived from a serotype between 1 and 50 with genetic mutations in the VA RNAs genes that confer selective replication on tumor cells.

Yet another objective of this invention is the use of an adenovirus for the treatment of cancer wherein said adenovirus is a human adenovirus derived from serotype 5.

This invention describes the use of mutant adenoviruses from VA RNA genes in cancer treatment. The VA RNA mutation allows replication of the adenovirus subject to the existence of an active Ras pathway or on the lack of PKR activation due to insensitivity to interferon. The invention is aimed at the need to find better treatments for pancreatic cancer, colon cancer, lung cancer, and other types of tumors.

This invention comprises adenoviruses that contain mutations in their genome that eliminate the PKR inactivating function of the associated-virus (VA) RNAs. There are two genes that encode VA RNAs in the genome of the adenovirus, VAI and VAII, located at approximately 30 map units on the viral genome. Both produce a short RNA (of some 160 ribonucleotides) synthesized by an RNA-polymerase III in the late phase of the viral cycle. Each VA RNA is folded in the shape of a loop that is bound to an RNA-dependent kinase, PKR. For the purpose of propagation, the adenovirus uses the VA RNAs to inhibit PKR, since otherwise this kinase phosphorylates the translation factor of eIF2 proteins, inactivating it and blocking protein. synthesis overall. Therefore, the VA mutants described in this invention are poorly propagated in normal cells. Conversely, these mutants are propagated normally in cells where the PKR is inactivated by the Ras pathway, as happens in many tumor cells. The VA mutants are also propagated normally in cells that do not respond to infection with PKR-inducing adenovirus.

The mutations of VA RNAs of this invention may affect the VAI and VAII genes. Alternatively or simultaneously, the mutations may affect the promoters of the VAI or VAII genes or their transcription termination sequences to block their expression.

VA mutant adenoviruses are propagated and amplified in cell lines with the active Ras pathway such as the human pancreatic carcinoma line NP9. After amplification in cell cultures, the mutants are extracted and purified according to standard methods in the adenovirology field.

The cancer treatment is performed by direct injection of the VA mutant into the tumor or by routine intravenous administration in cancer patients using standard methods in the field of adenovirus gene therapy.

DESCRIPTION OF THE DRAWINGS

The drawings included in the invention are attached for the purpose of showing the characteristics, advantages, and constructions of the invention so that they are clear and understood in detail. Those drawings form part of the specifications and illustrate the preferred inventions, but should not be considered to limit the scope of the invention.

FIG. 2: Sequence of the Ad5 VA Region. The DNA sequence shown (SEQ ID NO:2) corresponds to base pairs 10,500 to 11,100 of the adenovirus serotype 5 genome. This sequence contains 25 the VA region (only the strand in the direction of the VA genes is shown). The sequence shown goes from base pairs (bp)-118 in relation to the beginning of the transcription of the VAI gene to 64 bp beyond the termination point of the VAII. The VAI gene (160 bp) from the beginning to the end of the transcription is underlined and italicized. A sequence of 96 bp separates the VAI and VAII encoding sequences. VAII (161 bp) is found after VAI and is shown underlined and bold.

FIG. 4: Effect of Ras Activation on the Propagation of VA RNA mutants. Graph showing the production of virus in 293 (replication, day 2). Cell line 293 shows low levels of activated Ras. A plasmid containing an expression cassette of a negative dominant mutant of Ras (RasN17) was transfected to 293 and the propagation efficiency of a VAI RNA mutant adenovirus (dl331) was evaluated. The Ras inhibition that can be seen in the Western Blot is able to inhibit dl331 propagation. Conversely, when 293 was transfected with a plasmid containing an expression cassette of a constitutively active Ras mutant (RasV12) Ras activation by Western Blot and an increase in dl331 propagation were observed.

DETAILED PRESENTATION OF THE MODES OF EMBODIMENT

Structure of the Adenoviruses with Mutated Virus-Associated (VA) RNAs.

This invention describes the use of adenoviruses with mutated (i.e., functionally defective) virus-associated (VA) RNA-encoding genes for cancer treatment. The treatment is based on the selective replication of VA mutants in cells with an active Ras pathway.

In addition, tumors resistant to the antiviral effects of interferon (alpha, beta, and gamma interferons) can also be treated with these mutants. The mechanisms that allow this active-Ras- or interferon-resistance-dependent replication are detailed below. In the cytoplasm of adenovirus-infected cells, large quantities of small RNAs called virus-associated (VA) RNAs were detected. These RNAs are synthesized by cellular RNA polymerase III by transcribing some adenovirus genes located at approximately 30 map units on the adenovirus genome. Some adenovirus serotypes contain only a VA gene (those belonging to subgroups A and F, and some serotypes from subgroup B) while others contain two VA genes (VAI and VAII are present in some serotypes of subgroup B and in all serotypes of subgroups C, D, and E).

Figure 1:
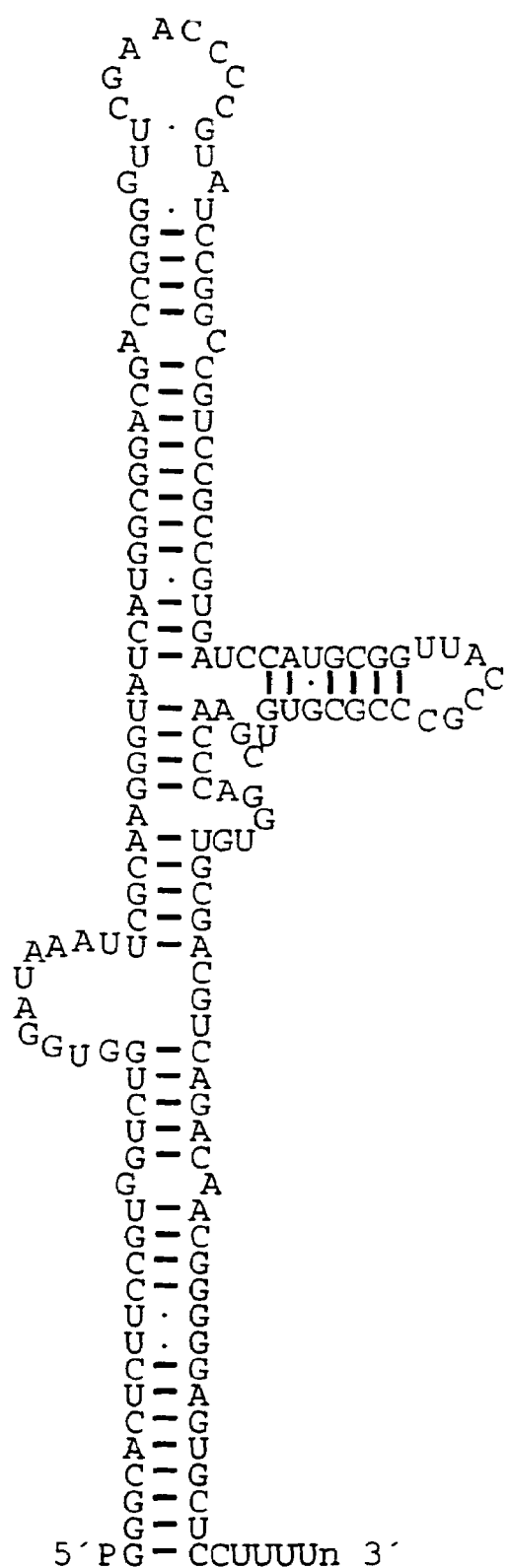
FIG. 1: Secondary VAI RNA Structure of the Adenovirus Serotype 5 (Ad5) (SEQ ID NO:1). A structure of stems and loops formed by the pairing of bases according to Watson and Crick's pairing rules. The central domain is critical to the VA function and the apical stem is also involved in the interaction of VA1 RNA with PKR.
Figure 3:
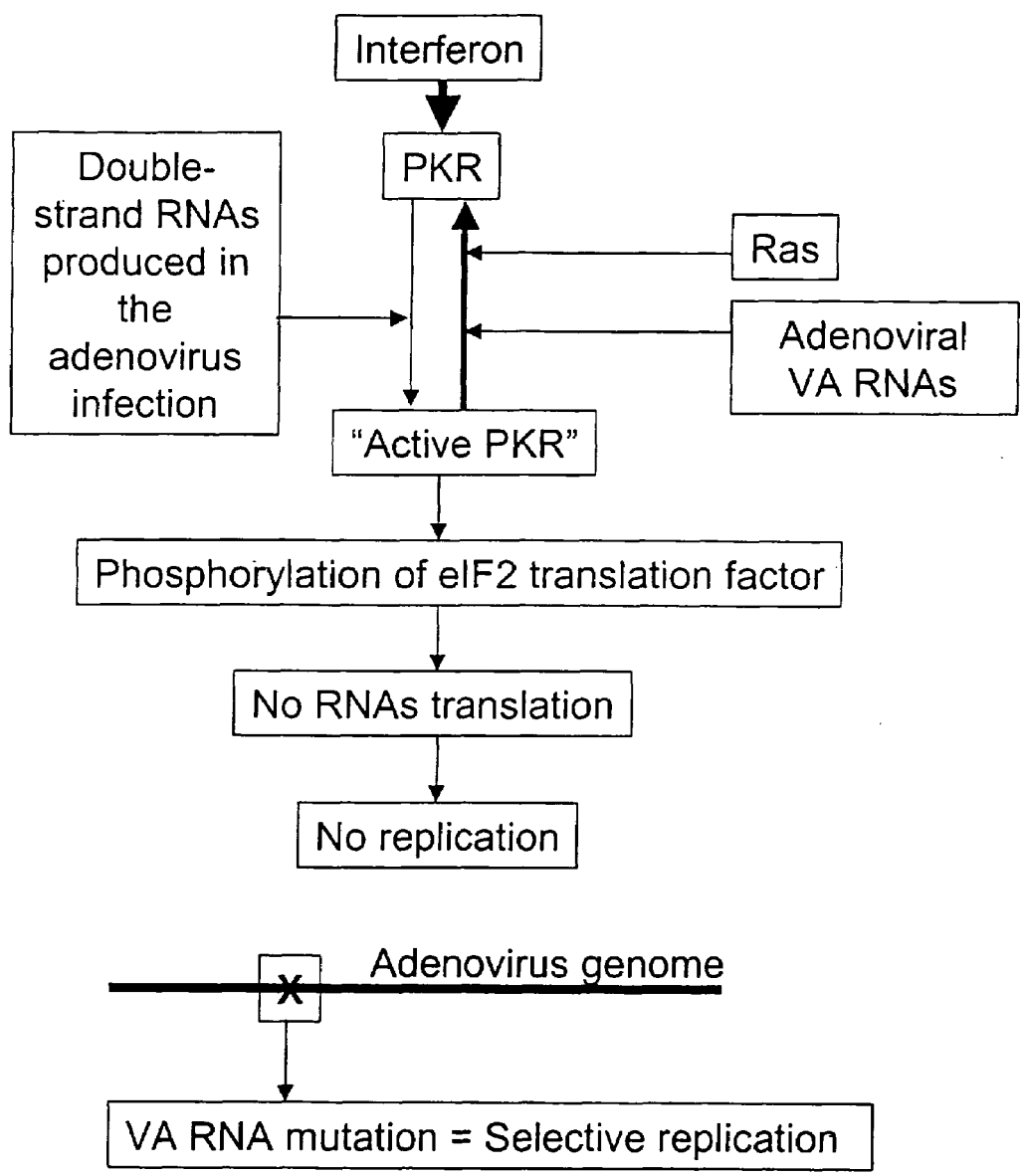
FIG. 3: Replication Selectivity Mechanism of Adenovirus with VA RNA Defects in Cells with Active RAS Pathway or Unresponsive to Interferon. Mechanism whereby virus-associated (VA) RNA mutants show replication subject to Ras activation. Adenoviral infection produces double-strand RNAs that induce PKR activation by phosphorylation. The activated PKR phosphorylates the translation factor of eIF2 proteins and inactivates it, thus blocking the overall transduction of proteins. The VA RNAs of the adenovirus bind with and inactivate the PKR to counteract this antiviral response of the infected cell. The VA RNA mutant adenoviruses cannot inhibit PKR and prevent the overall block of protein synthesis. In addition, activation of the oncogenic Ras also inhibits PKR and when it is active, the VA mutants are propagated normally.

The VA RNAs have some 160 ribonucleotides and form a secondary structure characterized by double-strand stems and single-strand loops (see FIG. 1). This VA RNA competes in binding to a protein kinase called PKR with other double-strand RNAs produced during the adenovirus infection. PKR is a kinase protein whose phosphorylating activity is dependent on double-strand RNA; however, the bond with VA RNA inhibits it rather than activating it. This function of the VA RNAs is necessary for viral replication since the activated PKR phosphorylates the initiation factor of the eIF2 protein transduction, inactivating it and blocking protein synthesis. In addition, PKR inhibition by Ras has been described (Mundschau and Faller, Journal Biological Chemistry, 1992, Vol. 267, pp. 23092-8). With regard to PKR inhibition, the Ras transduction pathway that is found activated in a large number of tumors is functionally similar to the VA RNAs. Connecting these observations, this invention establishes that in tumor cells with an active Ras pathway, the VA RNA functions can be eliminated without affecting viral replication. The invention therefore describes that the VA RNA mutants can be used to treat tumors.

The selective replication mechanism in tumors of the VA mutants described in the above paragraph is based on the fact that the Ras effectors inactivate the PKR. In many tumors we also found another mechanism that stops PKR activation: the lack of response to interferon. The secretion of alpha, beta, or gamma interferon (IFN) is the innate immune system's first response to the virus. IFN induces PKR expression and the VA RNA genes of the adenovirus antagonize the antiviral effects of IFN by inhibiting PKR. In cells that do not respond to interferon, PKR is not induced and the quantity of PKR in the cytoplasm remains at very low levels. The VA RNA genes are then no longer necessary for viral replication. It is well established that tumor cells have defects in response to IFN. In fact, a virus that is very sensitive to the inhibitory effects of IFN has been used for the selective lysation of tumor cells and treatment of tumors (Stojdl et al., Nature Medicine 2000, Vol. 6, pp. 821-5). Connecting these observations to the embodiment of this invention is the use of VA RNA mutant adenoviruses to treat tumors with defects in the interferon pathway.

The VA RNA gene sequence of the adenovirus serotype 5 appears in FIG. 2. The VAI gene of the adenovirus 5 consists of 160 base pairs from base pair 10,620 to base pair 10,779 in the adenovirus genome sequence. The VAII gene consists of 161 base pairs from base pair 10,876 to 11,036. One embodiment of this invention contains a deletion within these sequences. Other embodiments contain deletions that affect sequences around these and that control the expression of the VA genes. In particular, sequences of 30 base pairs before the VA genes have been described as involved in regulating said expression (Fowlkes and Shenk, Cell 1980, Vol. 22, pp. 405-13). Another embodiment has deletions of the sequences after the VA genes that control the termination of its transcription by means of RNA polymerase III (Gunnery et. al., Journal of Molecular Biology 1999, Vol. 286, pp. 745-57).

During the VA RNA function study, several mutants were constructed that eliminate its function. This invention establishes that the previously established VA gene mutants that eliminate its PKR-inhibitory action can be used to treat cancer. New VA RNA mutants can also be used for the application described in this invention. There are several ways to manipulate the adenovirus genome. VA mutants can be constructed for example, by directed mutagenesis using protocols previously published by the inventors, but instead of using adenovirus fragments of the hexon or fiber described there, it uses a fragment that contains the VA genes. The procedure can be as follows: obtain purified DNA from adenovirus type 5 through SDS-proteinase K using standard methods. This viral DNA is cut with the Kpn I restriction enzyme and a fragment of 2749 bp (Ad5 bp #8,537-11,286) containing the VA RNA genes purified using gel electrophoresis. This fragment is cloned by binding it to digested pUC19 plasmid with the same restriction enzyme. Directed mutagenesis to detect any of the VA sequences indicated above is done on this plasmid using commercial protocols ("Quick Change site-directed mutagenesis kit," Stratagene, La Jolla, Calif.). The mutated Kpn I fragment is then introduced into the viral genome by homologous recombination using a plasmid containing the complete Ad5 genome partially digested with Rsr II (the target in bp 10,944 is repaired via homologous recombination). From the resulting plasmid the VA mutant is obtained by transfection in 293 cells or cells with an active Ras pathway.

Further types of genetic mutations and manipulations other than the VA RNA gene mutations described in this invention have been performed to obtain selective replication in tumors. These may be insertions of promoters that are active in tumor cells to control viral gene expression and deletions of early functions ("early E1 and E4) that block the RB or p53 pathways. One embodiment of this invention is the use of mutations in the VA RNA genes in combination with those other manipulations to obtain selective replication in tumors.

In another embodiment of the invention the VA RNA mutants can have modifications to their capsids to increase their infectivity or direct them to receptors present in the tumor cell. The proteins of the adenovirus capsid have been genetically modified to include ligands that increase infectivity or direct the virus to a receptor in the tumor cell. Directing the adenovirus to the tumor may also be achieved with bifunctional ligands that bind to the virus on one side and to the tumor receptor on the other. In addition, the capsid may be covered with polymers such as polyethylene glycol in order to increase the persistence of the adenovirus in blood and increase the chances of reaching disseminated tumor nodules. These modifications can be configured in VA RNA mutants. Another embodiment of this invention is the use of VA RNA mutants of adenovirus serotypes other than Ad5. Of the more than 50 human adenovirus serotypes, there are at least 47 serotypes in which the VA RNA gene sequence is well defined (Ma and Mathews, Journal of Virology 1996. Vol. 70, pp. 5083-99). The mutation of the VA genes in those serotypes can be used to obtain replication subject to active Ras or resistance to interferon.

Another embodiment of this invention describes the use of VA RNA mutant adenoviruses containing other genes to increase cytotoxicity on tumor cells such as the thymidine kinase or cytosine deaminase gene, proapoptotic genes, immunostimulants, or tumor suppressants.

Production, Purification, and Formulation of VA RNA-Mutated Adenovirus.

VA RNA mutant adenoviruses are propagated according to standard methods in the fields of adenovirology and adenoviral vectors. The preferred method of propagation is by infecting a cell line that allows replication of VA RNA mutants. Said line has a mutated or active Ras oncogene, for example. The NP9 pancreatic carcinoma line is one example of said line. The propagation is performed in the following way, for example: The NP9 cells are grown on plastic cell culture plates and infected using 50 viral particles per cell. Two days later, the cytopathic effect showing virus production appears as a cluster of cells. The cells are gathered and stored in tubes. After centrifugation at 1000 g for 5 minutes, the cellular precipitate is frozen and thawed three times to break the cells. The resulting cellular extract is centrifuged at 1000 g for 5 minutes and the supernatant with virus is loaded on top of a cesium chloride gradient and centrifuged for 1 hour at 35,000 g. The virus band in the gradient is loaded again on another cesium chloride gradient and centrifuged for 16 hours at 35,000 g. The virus band is collected and dialyzed against PBS-10% glycerol. The dialyzed virus is aliquoted and stored at −80° C. The quantification of the number of plaque-forming particles and units is performed according to standard protocol. A saline phosphate buffer with 10% glycerol is a standard formulation for the storage of adenovirus.

Use of VA RNA Mutant Adenoviruses in Cancer Treatment.

This invention describes the use of adenoviruses with defects in the VA RNA genes to treat cancer. The treatment is based on the selective replication of VA RNA mutants in cells with an active Ras pathway or resistant to the effects of interferon.

The protocols for using VA mutants in cancer treatment follow the same procedures as those used in the fields of adenovirus therapy and adenovirus gene therapy. There is extensive experience in the use of nonreplicative and replicative adenoviruses in the field of gene therapy. In particular, adenoviruses with selective replication mechanisms different from those proposed in this invention have been used to treat cancer. There are numerous publications on the treatment of tumor cells in culture, in animal models, and in clinical trials with patients. For the treatment of culture cells in vitro, the purified adenovirus in any of the formulations described above are added to the culture medium to infect the tumor cells. To treat tumors in animal models or human patients, the adenovirus may be administered locoregionally by injecting it into the tumor or into a body cavity where the tumor is located, or systematically by injection into the bloodstream. As has been practiced with other selective replication adenoviruses, the treatment of tumors with the VA RNA mutants described in this invention may be combined with other treatment modalities such as chemotherapy or radiation therapy.

EXAMPLE 1 a Mutated Adenovirus In the VAI Gene Shows Ras-dependent Replication

To demonstrate the dependence of the replication of a VAI RNA mutant (dl331) on an activated Ras pathway we have modulated the activation status of Ras in human cells. Approximately $1.0 \times 10^7$ embryonic human kidney cells (line 293) are seeded on a plate 10 cm in diameter and transfected with 24 micrograms of plasmids containing either green fluorescence protein (GFP), the constitutively active form of Ras (H-Ras V12) or the negative dominant of Ras (H-Ras N17). A standard protocol of calcium phosphate was used for the transfection. Forty-eight hours after transfection the cells were transferred to new plates. To demonstrate the effect of transfection of the plasmids on the Ras pathway, we looked at the expression levels and phosphorylation of ERK (a Ras effector) on a cellular lysate by Western Blot. The dry lysate was obtained through incubation with a lysis buffer (20 mM Tris, 2 mM EDTA, 100 mM NaCl, 5 mM $MgCl_2$, 1% Triton X-100, 10% glycerol, 5 mM NaF, 100 microM $Na_3VO_4$), 1 mM PMSF, 10 µg/ml aprotinin, 10 µg/ml leupeptin) for 1 hour at 4° C. After centrifuging at 14,000 g, the supernatant proteins (10 micrograms per track determined using a Bradford assay) were separated electrophoretically in a 10% polyacrylamide-SDS gel, and transferred to a PVDF membrane. The amount of ERK and phospho-ERK was revealed using Amersham's chemoluminescence kit (ECL). As primary antibodies, a monoclonal antibody (Ab) against ERK (Zymed) or a polyclonal antibody against phospho-ERK (Cell Signaling Tech.) were used. Mouse anti-IgG or rabbit anti-IgG conjugated with radish peroxidase were used as secondary antibodies. Following these procedures we demonstrated that the untransfected 293 cells have a low level of ERK phosphorylation, indicating a low Ras pathway activity. The control transfection with GFP did not affect these results. Transfection with H-Ras V12 increased ERK phosphorylation indicating activation of the Ras pathway. In contrast, transfection with H-Ras N17 results in the inhibition of the Ras pathway. (FIG. 4 of the invention, top panel).

Once modulation of the Ras pathway was verified according to the above procedures we proceeded to demonstrate the selective replication of VA RNA mutants as described below. The transfected cells, as described in the above paragraph, were infected with the VAI RNA mutant dl331 or with wild-type adenovirus using 10 plaque-forming units per cell. Virus production was analyzed each day by measuring the quantity of adenovirus in the supernatant by means of plaque formation assays on 293. The wild-type adenovirus replicated 7 to 10 times better than the VAI mutant in control 293 cells or cells transfected with GFP. The activation of the Ras pathway induced by H-Ras V12 increased the replication efficiency of the VA mutant by 10 times, so that its replication level reached the level of wild-type adenovirus. Conversely, inhibition of the Ras pathway with H-Ras N17 decreased the replication of the VA mutant by 2 times. Therefore, compared with the replication of the wild-type adenovirus, replication of the VAI RNA mutant is 20 times more dependent on RAS pathway activation than we realized.

EXAMPLE 2

Figure 5:
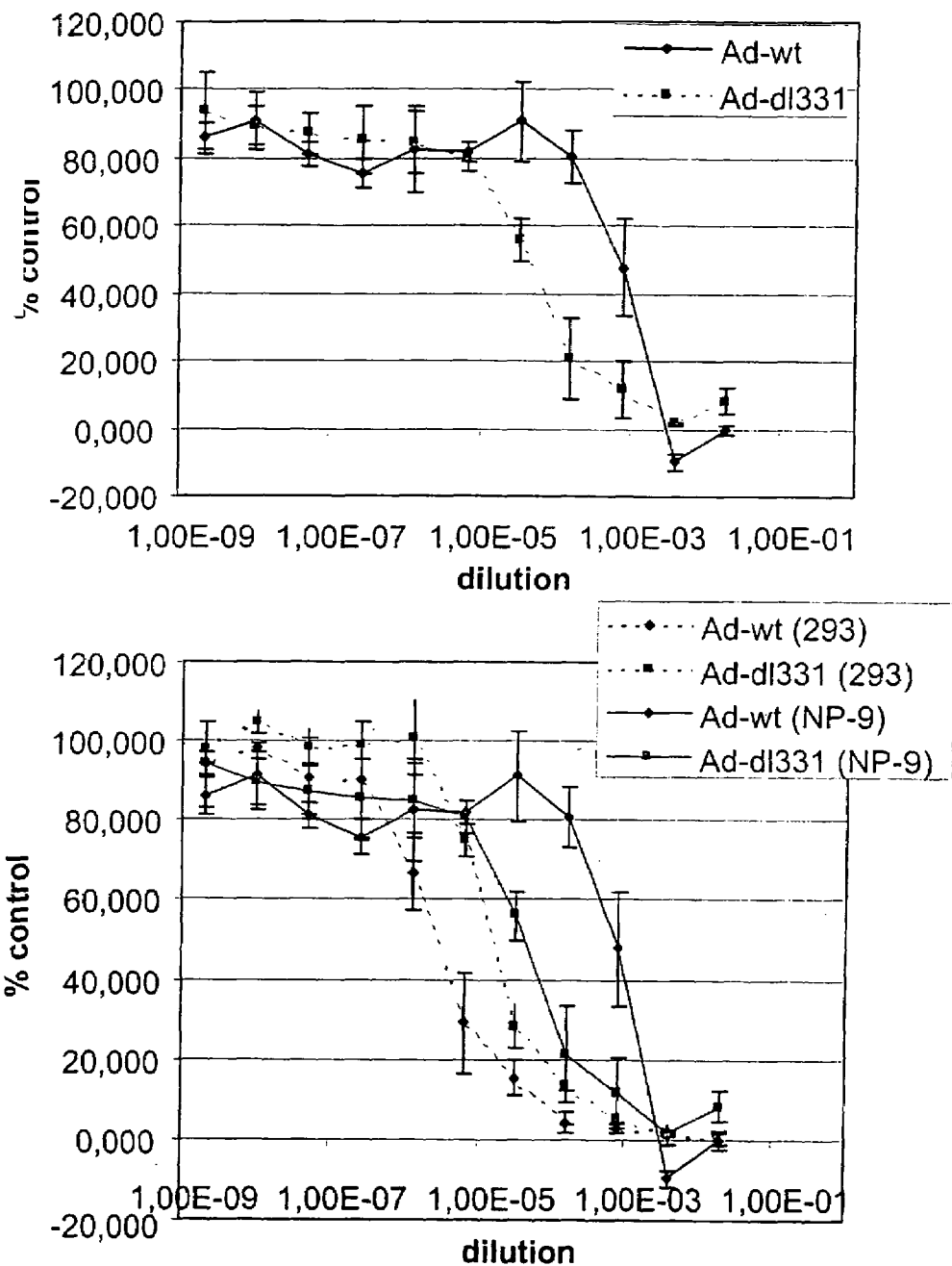
FIG. 5: Propagation of a VA RNA Mutated Adenovirus in Cells with Low (293) or High (NPA) Ras Activity. Graph of the cytopathic effect (CPE) quantified by BCA (day 5). Comparison of the propagation of VA RNA mutants in cells with low Ras activity and pancreatic cancer cells with high levels of active Ras. The propagation of the wild-type adenovirus Ad5 is used as a standardization control to correct differences in infectivity and replication that cannot be attributed to VA mutation.

Human Tumor Cells with Active Ras Pathway Allow for Efficient Replication Of an Adenovirus with Mutated VAI RNAs Replication of a mutated adenovirus in the VAI RNA gene (dl331) was quantified in the NP9 human pancreatic cancer line that has a mutation in codon 12 of the K-Ras gene (GGT→GAT). Replication is estimated by the cytopathic effect (CPE) that the virus induces measured as a decrease in the quantity of protein in the cellular monolayer (BCA method). In short, the NP-9 cells are seeded on 96-well plates with 30,000 cells per well. On the next day the cells are infected with serial dilutions of dl331 or wild-type adenovirus from a concentration of 1000 plaque-forming units per cell. The infected cells are incubated for 5 days and the culture medium is removed to measure the quantity of protein remaining in the well. FIG. 5 shows the results obtained as the percentage of protein with respect to the uninfected wells compared to the dilution of the viral inoculum. The dilution that produces 50% mortality (50% reduction in the protein content, IC50) is an estimate of the oncolytic potency of the initial virus preparation. In cells with a mutated Ras (NP9) the IC50 obtained for the VAI RNA mutant dl331 and for the wild-type adenovirus is 0.04 and 0.7, respectively, indicating an potency increase of the VAI RNA mutant by 18 times (FIG. 5, top panel and continuous line of the bottom panel). In cells with low Ras activity (293) these values were 0.018 and 0.003 indicating a potency decrease of the VAI RNA by 6 times. As a whole, the results show that if we compare the oncolytic potency of a VAI RNA mutant to the wild-type adenovirus in cells with active Ras or in cells with almost inactive Ras, Ras activation increases the replication of the VAI mutant by around 100 times.

Figure 6:
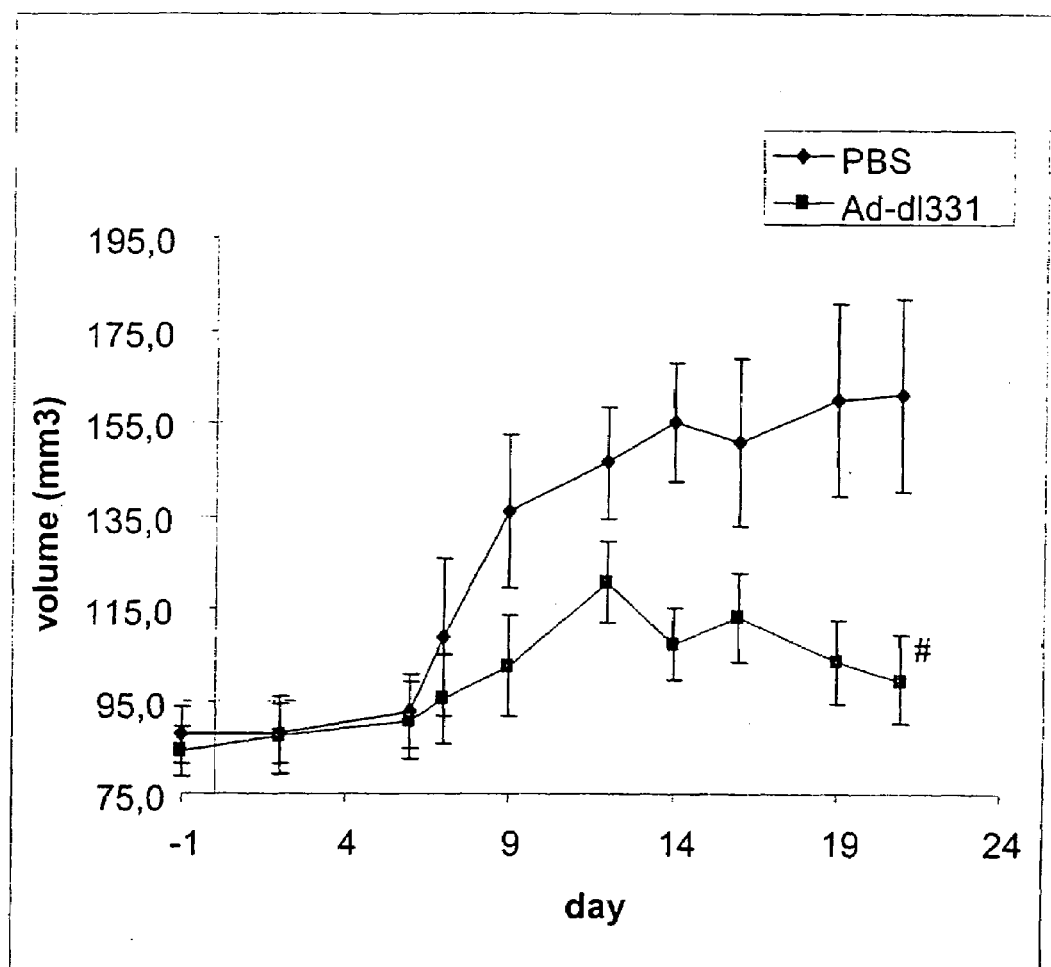
FIG. 6: Treatment of Tumors with a VA RNA Mutant. NP9 human pancreatic cancer tumors were implanted in immunosuppressed mice (Balb/c nude mice). When the tumors reached a volume of 70-80 $mm^3$ they were injected with a VAI RNA mutant adenovirus (dl331) or with a control vehicle. After measuring tumor progression (volume of the tumor) the antitumor effect of the VA RNA mutant was demonstrated.

EXAMPLE 3 a Mutated Adenovirus In the VAI RNA Gene can be Used to Treat Tumors Effectively Below we will demonstrate the antitumor effect of a VAI RNA mutant adenovirus (dl331). An in vivo experiment was performed with athymic mice of the Balb/c strain that contained tumors with an activated Ras pathway (NP9). All the experiments were performed according to FELASA guidelines (Federation of European Laboratory Animal Science Associations). A total of 1.2×107 tumor cells of the NP-9 cell line were injected subcutaneously in each posterior flank of the mouse. After 1 day the tumors formed (which reached 70-80 mm$^3$) were distributed between different experimental groups (n=10 per group). The tumors of the control group received two intratumoral injections of saline buffer (2×10 µl). Those in the group treated with the VA mutant received two intratumoral injections (2×10 µl) of dl331 (109 viral particles per tumor). FIG. 6 shows the tumor volume compared to the initial treatment (day 0). The results are presented as mean ±S.E.M. The existence of significant differences between the results was calculated using a non-parametric, non-paired data Mann-Whitney U test. The growth curves were compared using a variance analysis. The results were considered significant if $p<0.05$. The calculations were done with an SPSS statistical package (SPSS Inc., Chicago, Ill.). There is a significant difference between tumor size on days 16 and 21. The tumors treated with the VAI RNA mutant dl331 showed regression.

The invention claimed is:

1. A method of treating cancer comprising administering, to a subject having cancer, an adenovirus having mutated VAI and VAII RNA genes, wherein said adenovirus is defective in its VAI and VAII virus-associated RNAs and will selectively replicate in cells of said cancer.

2. The method according to claim 1, wherein said adenovirus further has mutations in one or both of E1a or E1b to obtain selective replication in tumors.

3. The method of claim 2, wherein said mutation in one or both of E1a or E1b is a mutation in a promoter region.

4. The method according to claim 1, wherein said adenovirus has mutations in the VA RNA genes to obtain selective replication in tumor cells with an active Ras pathway or unresponsive to interferon.

5. The method according to claim 1, wherein said adenovirus further has at least one modification in its capsid to increase its infectivity or to direct it to a receptor present on a tumor cell.

6. The method according to claim 1, wherein said adenovirus has mutations in the VA RNA genes that confer selective replication in tumor cells and further comprises at least one other gene useful in cancer gene therapy.

7. The method according to claim 6, wherein the gene useful in cancer gene therapy is selected from the group consisting of prodrug activators, tumor suppressors, and immunostimulants.

8. The method according to claim 1, wherein said adenovirus is a human adenovirus derived from a serotype between 1 and 50, inclusive, that has both a VAI gene and a VAII gene.

9. The method according to claim 8, wherein said adenovirus is a human adenovirus derived from serotype 5.

10. The method of claim 1, wherein the subject is a human.

11. The method of claim 1, wherein said adenovirus further has at least one mutation in one or more genes of the group E1a, E1b, and E4, wherein said mutation is an insertion of a promoter that is selectively active in tumor cells.

12. The method of claim 1, wherein the cancer cells have an active ras pathway.

13. The method of claim 1, wherein the cancer cells are unresponsive to interferon.

14. The method of claim 1, wherein the adenovirus is a human adenovirus.

15. A method of treating cancer comprising administering, to a subject having cancer, an adenovirus comprising:
   (A) one or a combination of (i) a mutation within a VAI gene; (ii) a mutation in a sequence before a VAI gene that controls the expression of said gene; or (iii) a mutation in a sequence after a VAI gene that controls termination of transcription of said gene, and
   (B) one or a combination of (i) a mutation within a VAII gene; (ii) a mutation in a sequence before a VAII gene that controls the expression of said gene; or (iii) a mutation in a sequence after a VAII gene that controls termination of transcription of said gene, wherein said mutations result in defective VAI and VAII virus-associated RNAs, and wherein said adenovirus will selectively replicate in cells of said cancer.

* * * * *

UNITED STATES PATENT AND TRADEMARK OFFICE
CERTIFICATE OF CORRECTION

PATENT NO. : 7,344,711 B2  Page 1 of 1
APPLICATION NO. : 10/509194
DATED : March 18, 2008
INVENTOR(S) : Bonastre et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 346 days Delete the phrase "by 346 days" and insert -- by 354 days --

Signed and Sealed this

Tenth Day of March, 2009

JOHN DOLL
*Acting Director of the United States Patent and Trademark Office*